United States Patent [19]

Louiday

[11] Patent Number: 4,550,421
[45] Date of Patent: Oct. 29, 1985

[54] RADIOLOGY TABLE FOR EXPOSURES WITH VARIABLE TILTING ANGLE AND SOURCE-PATIENT DISTANCE AND FOR TOMOGRAPHY

[75] Inventor: André E. Louiday, Le Pecq, France

[73] Assignee: U.S. Philips Corporation, New York, N.Y.

[21] Appl. No.: 593,185

[22] Filed: Mar. 26, 1984

Related U.S. Application Data

[63] Continuation of Ser. No. 387,123, Jun. 10, 1982, abandoned.

[30] Foreign Application Priority Data

Jun. 12, 1981 [FR] France ................................ 8111621

[51] Int. Cl.⁴ .............................................. G03B 41/16
[52] U.S. Cl. ....................................... 378/196; 378/26
[58] Field of Search .................... 378/25, 26, 196, 195

[56] References Cited

U.S. PATENT DOCUMENTS 3,733,487  5/1973  Louche ................................. 378/91
4,213,050  7/1980  Meek ..................................... 378/91

FOREIGN PATENT DOCUMENTS 1569601  11/1967  France ................................. 378/26

Primary Examiner—Craig E. Church
Attorney, Agent, or Firm—Marc D. Schechter

[57] ABSTRACT

The invention relates to a radiology table in which a column carrying an X-ray source is telescopic and can be tilted relative to the patient plane. In the table according to the invention, the tilting movement and length variation of the column are obtained by means of a single motor carried by the base of the column. The output shaft of this motor carries a crank, whose crank pin simultaneously follows a stationary guide on the table frame and a guide 6 connected to the telescopic part of the column.

7 Claims, 6 Drawing Figures

RADIOLOGY TABLE FOR EXPOSURES WITH VARIABLE TILTING ANGLE AND SOURCE-PATIENT DISTANCE AND FOR TOMOGRAPHY

This is a continuation of application Ser. No. 387,123, filed June 10, 1982 now abandoned.

BACKGROUND OF THE INVENTION

The invention relates to a radiology table which comprises a stationary or movable frame supporting a table top on which a patient is positioned. The table further includes a column carrying an X-ray source, and an image-receiver mount. The column comprises a tubular base of fixed length. The base of the column is mounted on the frame so as to be pivotable about a tilting axis perpendicular to the longitudinal axis of the column. The column also comprises a telescopic part carrying the X-ray source and being slidable inside the tubular base. The tilting angle of the column is variable and the length of the column between the tilting axis and the source is adjustable to a plurality of values. The length of the column may be varied independently of the tilting angle or alternatively as a function of the tilting angle in order to obtain a linear source path for tomographic scanning purposes.

Such a table is known from French Pat. No. 1,569,601. It is used in medical radiology, primarily for oblique exposures during which the X-ray source and the image-receiver (for example photographic film or an image intensifier) are stationary but aligned on an axis which is not perpendicular to the patient plane. This orientation is achieved by means of a first motor which tilts the column.

The table described in French Pat. No. 1,569,601 also permits radiographs to be made with various source-patient distances by means of a second motor, acting in fact as a jack which varies the length of telescopic column. Finally, the table permits body-section radiographs to be made by a suitable combination of the tilting angle and the length of the telescopic column, the linear displacement of the source being obtained by means of a suitable cam profile (which described in German Pat. No. 1,118,928).

The table according to French Pat. No. 1,569,601 requires the use of two motors arranged on the column. This is a heavy and expensive construction.

SUMMARY OF THE INVENTION

The present invention is a radiology table in which the tilting movement and the length variation of the column are obtained by means of a single motor carried by the tubular base of the column. The output shaft of the motor, which is parallel to and spaced from the tilting axis, carries a crank whose crank pin simultaneously follows (i) a stationary guide secured to the frame (for the purpose of tilting), and (ii) a guide which is connected to the telescopic part of the column (for the length variation). As a result of the combination of the two movements which the motor imposes, via the crank and its crank pin, on the base of the column and on the telescopic part, the source describes a closed path of which the various portions may be used for obtaining the aforementioned results.

Another drawback of the prior art discussed above is the need to use cams with geometrical profiles which are difficult to machine. In a special embodiment of the invention, the length-variation guide is a rectilinear slide which is perpendicular to the longitudinal axis of the column. The maximum extension of the column is equal to twice the crank radius.

In a further embodiment of the invention, the axis of the crank on the tubular base of the column is situated opposite the X-ray source with respect to the tilting axis, and the tilting guide on the frame is a rectilinear slide which is normal to the patient plane and whose axis intersects the tilting axis. The lever arm between the tilting axis and the crank axis is greater than the crank radius. A radiology table combining these two characteristic features can be constructed by means of guides machined simply in a straight line.

In such a table:
- $i$ is the tilting angle of the column relative to the normal to the patient plane,
- $j$ is the angle of the crank relative to its position in which it is parallel to the column when the extension is at a maximum,
- $c$ is the length of the sliding telescopic part of the column,
- $b$ is the length of the lever arm between the tilting axis and the crank axis,
- $m$ is the crank radius, and
- $R$ is the useful length of the column from the tilting axis to the X-ray source.

The polar coordinates of the path of the source in the plane of oscillation of the column, about the trace of the tilting axis, are R and i, which are related by the following mathematical expressions:

$$R = c - b + m \cdot \cos j \text{ and } \frac{m}{\sin i} = \frac{b}{\sin(i + j)}$$

which may be solved by eliminating the parameter j yielding:

$$R = c - b \cdot \cos^2 i - e \cdot \cos i \cdot \sqrt{m^2 - b^2 \cdot \sin^2 i},$$

where $e = \pm 1$, or by expansion (Maclaurin):

$$R = c - (1 + 2) \cdot b \cdot \cos^2 i - e \cdot (m - b) - e \cdot \frac{(m - b)^2}{2b} + e \cdot \frac{(m^2 - b^2)^2}{8b^3 \cdot \cos^2 i} \ldots$$

The maximum tilting angle, $i_{max}$, obtained by means of the column is $i_{max} = \arcsin(m/b)$. When the angle j of the crank relative to the column is between 0° and +90° or between +270° and +360° (or more simply between −90° and +90°), the X-ray source follows an "upper" branch of the path (cos j positive, $e = -1$). When the angle of the crank to the column is between +90° and +270°, the source follows a "lower" branch of the path (cos j negative, $e = +1$).

The upper branch of the path ($e = -1$) corresponds to a "radius" $R_h$ of the column which may be expressed as:

$$R_h = c + m - b + \frac{(m - b)^2}{2b} - \frac{(m^2 - b^2)^2}{8b^3 \cos^2 i} \ldots$$

This upper branch is similar to an arc of circle having a radius $(c + m - b)$, if the crank radius m differs only slightly from the length b of the lever arm (by about 0.6b or more).

The lower branch of the path (e=+1) corresponds to a column "radius" $R_b$ which may be expressed as:

$$R_b = c - m + b - 2b \cdot \cos^2 i - \frac{(m-b)^2}{2b} + \frac{(m^2-b^2)^2}{8b^3 \cdot \cos^2 i} \ldots$$

If the aforementioned requirement (0.6b<m<b) is met, this expression may be replaced by $R_b = c - m - b + 2b \cdot \sin^2 i$, to approximate the equation for a straight line parallel to the patient plane: $R_d = c - m - b/\cos i$. For small tilting angles ($|i|<25°$) the lower branch of the source path approximates this straight line, with a deviation of 1%, if the height c of the sliding part of the column is approximately $c \neq 5 \cdot b + m$.

DESCRIPTION OF THE PREFERRED EMBODIMENTS

Figure 1:
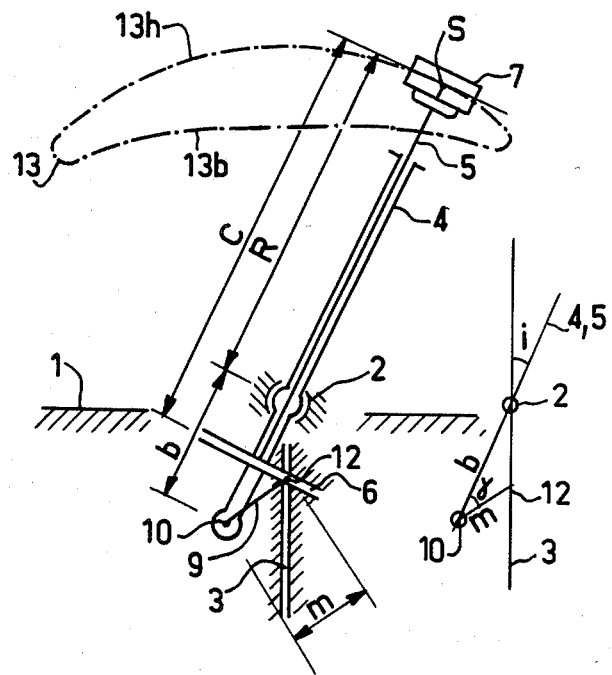
FIG. 1 is a simplified geometrical representation of a table according to the invention and its source-carrying column.

In FIG. 1 parts of the frame of the table are schematically represented by hatched portions. These are (a) the surface 1 of the table on which the patient is to be examined, which is shown in the horizontal position, (b) the pivot 2 of the column which has an axis parallel to the plane 1 (which axis is referred to as the tilting axis 2 of the column, and (c) a rectilinear slide 3, which is perpendicular to the plane 1, (vertical in the present case) and which is also perpendicular the tilting axis 2, and which assists in tilting the column, as will be explained hereinafter.

The tubular base 4 of a telescopic column carrying the X-ray source S is mounted for rotation about the pivot 2. A telescopic part 5 of the column, has an upper part which carries the source S. The lower part of telescopic part 5 projects from the closed part of the tubular base 4 (see FIGS. 2 and 3) and, carries a rectilinear slide 6. Slide 6 is perpendicular to telescopic part 5 and is disposed in the tilting plane of the column. Telescopic part 5 can slide inside the tubular base 4.

The source S, which is considered a point source, is situated in an X-ray tube. The X-ray tube is mounted in a casing 7 (called a "shield") which shields the X-rays. The shield 7 is disposed on the end of an arm 8 (FIGS. 2 and 3) which extends parallel to the pivot 2 and transverse to the column 4, 5. This means that the schematic view shown in FIG. 1 is the projection, parallel to the pivot 2, in a plane which extends through the source S and perpendicular to the pivot 2 (the tilting plane of the source).

Figure 2:
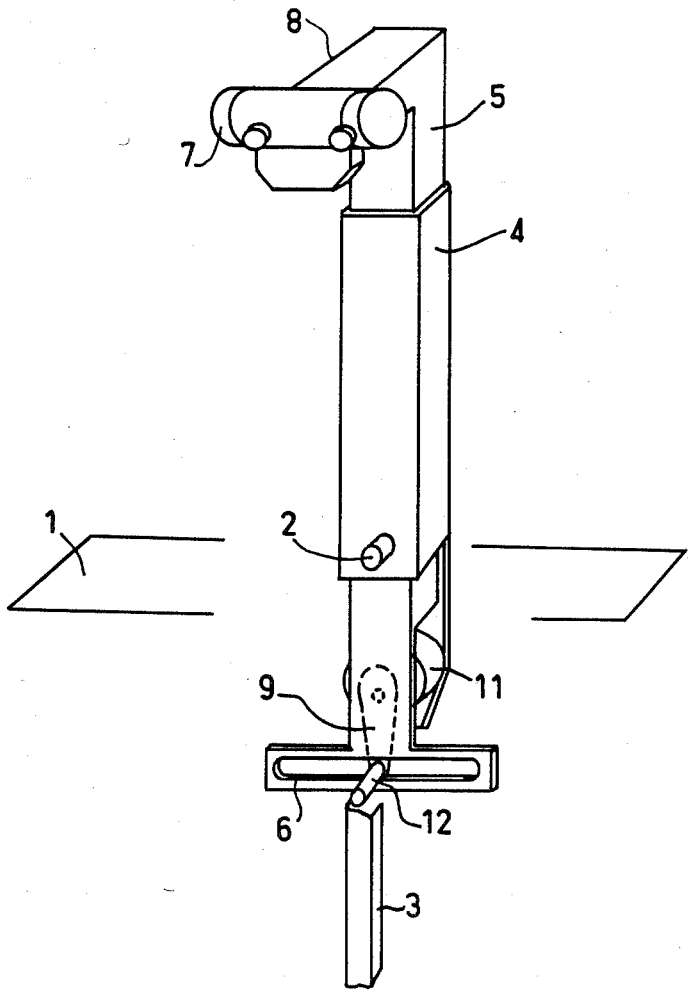
FIG. 2 is a schematic perspective view of the table shown in FIG. 1, the column being shown in a vertical position and the source being shown in the lower position.
Figures 3, 4:
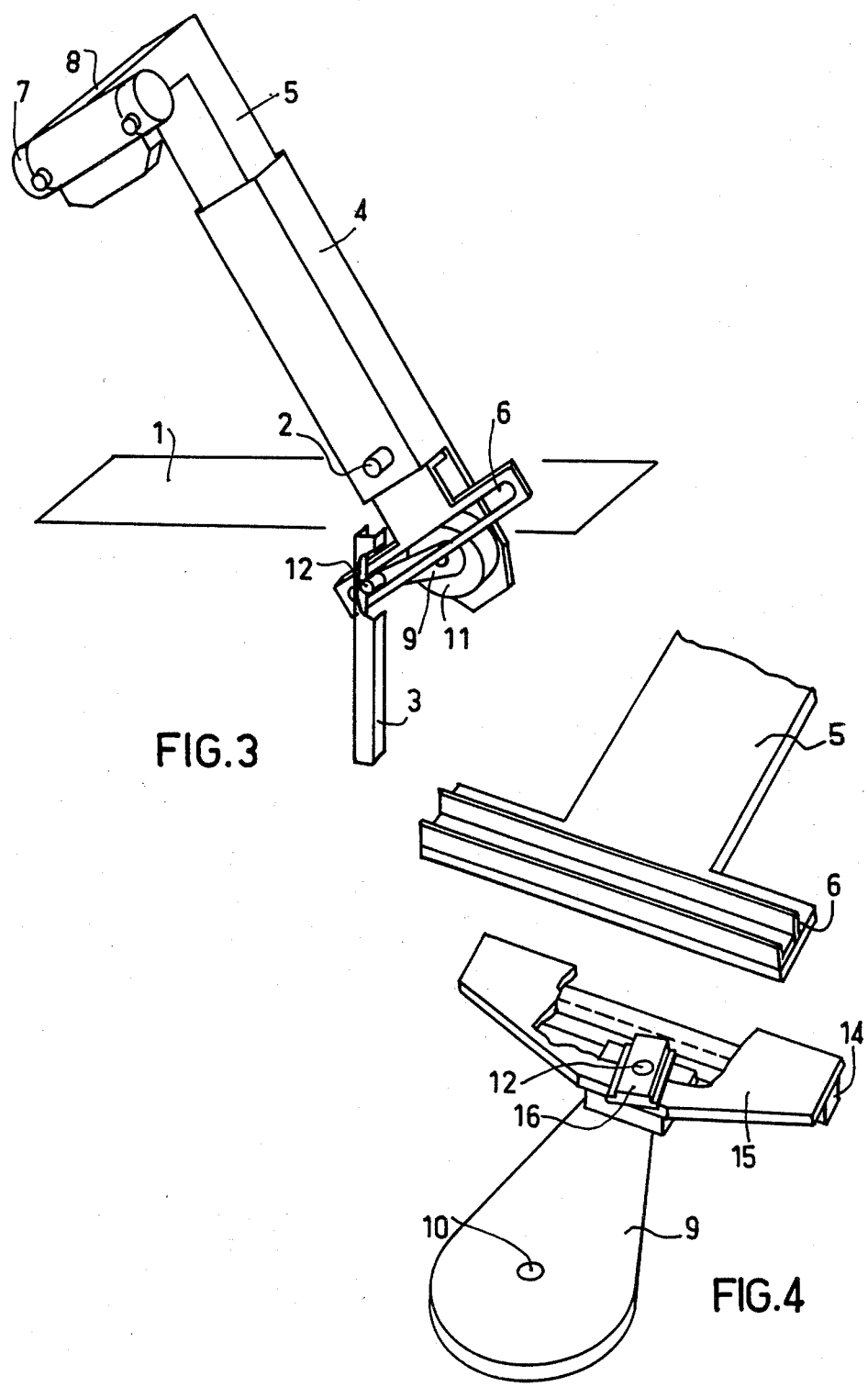
FIG. 3 is a schematic perspective view of the column of the table in an inclined position, the source being shown in the upper position.
FIG. 4 is a perspective view of the elements permitting the crank pin of the column shown in FIGS. 2 and 3 to follow two slides simultaneously.

At the lower end of the column on the tubular base 4 a crank 9 is mounted for rotation about an axis 10 parallel to the tilting axis 2. The crank 9 is driven by a motor 11, which is schematically shown in FIGS. 2 and 3 and which is secured to the tubular base 4 of the column. The mass of this motor partly balances the column whose telescopic part 5 carries the shield 7 which has a mass of about 40 kg. On the free end of the crank 9 a crank pin 12 is mounted. Crank pin 12 is shown as a simple cylindrical member in FIGS. 2 and 3. The pin 12 engages the two rectilinear guides 3 and 6 simultaneously.

The rotation of the crank 12 about its axis 10 produces an oscillation of the column 4, 5 about its tilting axis 2, and also produces an up and down movement of the telescopic part 5 of the column in its tubular base 4. The combination of these two movements results in a closed "banana"-shaped path 13 of the source 5, which path is indicated by the dashed-dot line in FIG. 1.

The mathematical explanation, above, applies to the embodiment described here. FIG. 1 also shows a simplified drawing, to scale, which more clearly shows the triangle (2, 12, 10) of which two angles i and j and two sides b and m are parameters which determine the path 13. The radiology table described has been constructed with the following dimensions: c=1500 mm, b=275 mm, m=200 mm. In this situation the maximum tilting angle of the column is ±46.6°.

When the crank makes an angle j=0 to the column, the sliding part 5 of the column is extended to its maximum extent. The source is then being situated at the apex of the upper branch ($13h$) of its path. The "radius" of the column is then $R_h$=1425 mm. This branch $13h$ resembles a circle of the radius $R_h$, with a deviation of 1%, through approximately ±40° to either side of the normal to the patient plane 1. Thus, the table enables radiographs to be made at all the tilting angles within this range.

When the angle of the crank 9 relative to the column 4, 5 is 180°, the column is fully retracted and the source is at the apex of the lower branch ($13b$) of its path. The "radius" of the column is then $R_b$=1025 mm. This branch $13b$ approximates a section of the straight line parallel to the patient plane 1, with a deviation of 1%, through approximately ±27° on either side of the normal to the plane 1. Thus, the table can be used for rectilinear scanning in this range.

Finally, when the column is perpendicular to the plane 1 it suffices to rotate the crank through 180° to pass from a source-patient distance of 1025 mm to a source-patient distance of 1425 mm and vice versa.

Certain details of the embodiment of the table whose operation has been described above are illustrated more clearly in FIGS. 4 to 6. FIG. 4 shows the crank 9 mounted on the motor shaft 10 and carrying the crank pin 12 on its end. This pin does not directly engage the rectilinear slides for the tilting and extension of the column but serves as a pivot for two members which are more suitable to perform this sliding movement.

The slide 6 comprises a U-shaped metal section which is secured to the base of the sliding part 5 of the column perpendicular to the column. The opening of the U extends transverse to the column. A rail 14 of corresponding, for example rectangular, cross-section engages the U-shaped section and is arranged on a bracket 15 which can be pivoted about the pin 12. This two-part slide 6 (which may also be arranged with the parts the other way around) enables the overall length of the slide at the base of the column to be reduced (in the schematic views shown in FIGS. 2 and 3 the length of the slide would be at least 2×m=400 mm). Satisfactory sliding properties are, for example, obtained by a phosphated steel slide section in combination with a bronze rail.

The slide 3 which determines the tilting angle of the column is of rectangular cross-section and receive a slide member 16 which, for example, is also made of bronze and which is also pivoted about the pivot 12. The slide member 16 and the bracket 15 are journalled on the pivot 12 by means of needle bearings.

Figure 5:
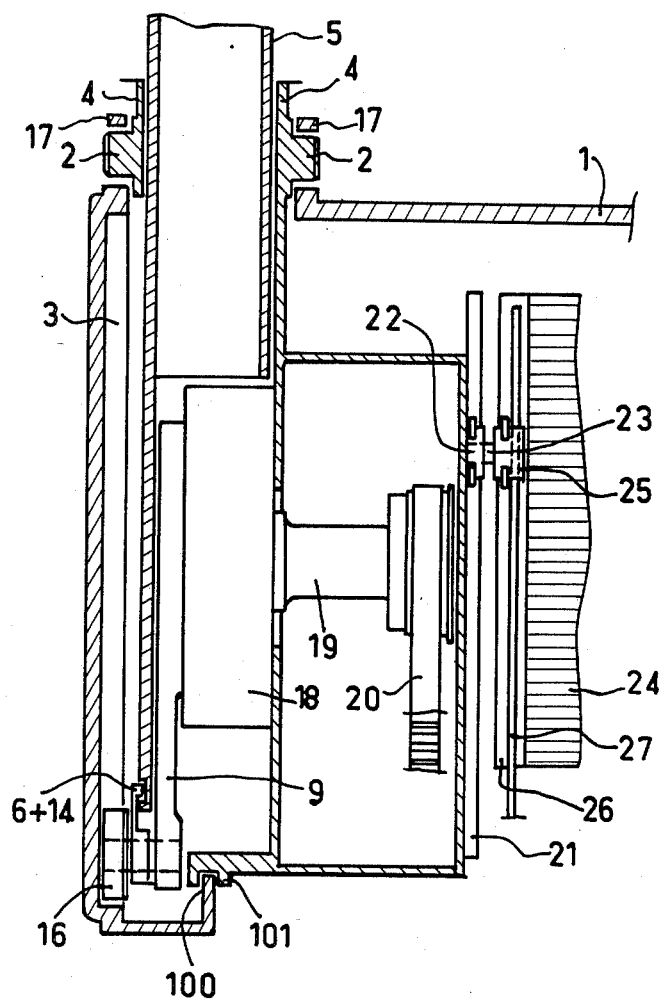
FIG. 5 is a longitudinal sectional view of the lower part of the column according to the invention.

FIG. 5 is a longitudinal sectional view of a part of the base of the column. The tubular base 4 carries two trunnions 2 which define its tilting axis and which are journalled in roller bearings. The roller bearings are secured to the table frame and to the table top 1 (bearings not shown). In order to improve the stability of the tilting plane of the column, a circular guide rail 100, which is rigidly connected to the table frame, co-operates with a guide 101, which is secured to a structural member of the tubular base 4 of the column, during movement of the column.

The crank 9 is mounted on the output shaft of a reduction gear 18 which may be of the deformable gear ring type (high reduction ratio). The input shaft 19 of this reduction gear is driven, via a pulley, by a toothed belt 20 which is rotated by a motor which is secured to the tubular base 4 of the column. The motor is not shown in the figure because it is offset relative to the column axis for construction reasons.

A vertical surface of the structural member which is parallel to the tilting plane and which supports the motor and the reduction gear cooperates with a slide 20 parallel to the column. The slide 20 is adapted to cooperate with a carriage 22 which pivots about a pivot 23 of the mount 24 for the radiographic-image receiver (called a "seriographic unit"). The pivot 23 itself is mounted on a slide member 25 whose height relative to the unit 24 is adjustable along a guideway 26, for example by means of a screw 27 parallel to the guideway and fitted into a threaded hole in the slide member 25.

Relative to the frame of the table, the unit 24 is mounted on rails which are parallel to the tilting plane of the column and to the patient plane 1 in such a way that it can travel over ±170 mm relative to its center position (column in the vertical position). Via coupling between the column and the seriographic unit provided by the pivot 23 the position of the image receiver (film or image intensifier) can be locked to the tilting movement of the column. By adjusting the height of the pivot 23 (via the screw 27) it is possible to adjust the height of a tomography "section" in the customary manner.

Figure 6:
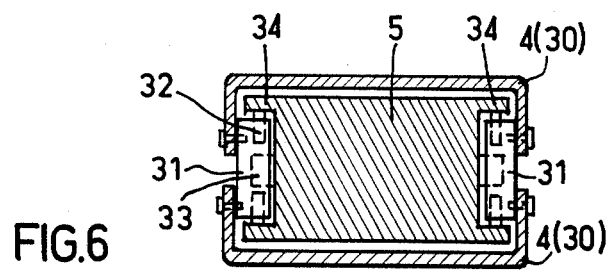
FIG. 6 is a cross-sectional view of the column.

FIG. 6 is a cross-sectional view of the column 4, 5. The tubular base 4 comprises two facing U-shaped sections (30) interconnected by parallelepiped internal connecting members 31, on three surfaces of which rollers 32 and 33 are mounted. The sliding part 5 of the column, which for the sake of simplicity is shown as a solid part, has U-shaped recesses in two surfaces. The openings of the recesses face the connecting members 31 for cooperation with the rollers 32 and 33, which permit the part 5 to be positioned and to slide in the base 4.

What is claimed is:

1. A radiology table comprising:

a frame;
    a table top supported by the frame;
    a column having a longitudinal axis, said column comprising a tubular base and a telescopic part slidable inside the tubular base along the longitudinal axis, said base having a fixed length and being mounted on the frame so as to be pivotable about a tilt axis which is perpendicular to the longitudinal axis, said column having first and second ends on opposite sides of the tilt axis;
    an X-ray source mounted on the telescopic part of the column at the first end of the column;
    a motor mounted on the tubular base of the column;
    a shaft having a shaft axis which is parallel to but spaced from the tilt axis, said shaft being rotatable about the shaft axis by the motor;
    a crank, rotatably mounted on the tubular base of the column for rotation around the shaft axis, said crank having a crank pin displaced from the shaft axis;
    a stationary guide secured to the frame and engaging the crank pin such that rotation of the crank causes the column to pivot about the tilt axis; and
    a movable guide connected to the telescopic part of the column and engaging the crank pin such that rotation of the crank pin causes the telescopic part of the column to slide within the tubular base of the column.

2. A radiology table as claimed in claim 1, characterized in that:

the column has maximum and minimum lengths; and
    the movable guide comprises a linear slide which is perpendicular to the longitudinal axis of the column, the maximum length of the column exceeding the minimum length of the column by twice the distance between the crank pin and the shaft axis.

3. A radiology table as claimed in claim 2, characterized in that:

the shaft axis is spaced from the tilt axis toward the second end of the column; and
    the stationary guide comprises a linear slide which is perpendicular to the table top and which intersects the tilt axis of the column, the distance between the shaft axis and the tilt axis being greater than the distance between the shaft axis and the crank pin.

4. A radiology table as claimed in claim 3, characterized in that:

the distance, m, between the shaft axis and the crank pin is no less than 0.6 times the distances, b, between the shaft axis and the tilt axis; and
    the length, c, of the telescopic part of the column is approximately equal to m plus the product of 5 times b.

5. A radiology table as claimed in claim 2, characterized in that:

the distance, m, between the shaft axis and the crank pin is no less than 0.6 times the distances, b, between the shaft axis and the tilt axis; and
    the length, c, of the telescopic part of the column is approximately equal to m plus the product of 5 times b.

6. A radiology table as claimed in claim 1, characterized in that:

the shaft axis is spaced from the tilt axis toward the second end of the column; and
    the stationary guide comprises a linear slide which is perpendicular to the table top and which intersects the tilt axis of the column, the distance between the shaft axis and the tilt axis being greater than the distance between the shaft axis and the crank pin.

7. A radiology table as claimed in claim 6, characterized in that:

the distance, m, between the shaft axis and the crank pin is no less than 0.6 times the distances, b, between the shaft axis and the tilt axis; and the length, c, of the telescopic part of the column is approximately equal to m plus the product of 5 times b.

* * * * *